United States Patent [19]

Konrad et al.

[11] 4,321,053
[45] Mar. 23, 1982

[54] HAIR DYEING COMPOSITION AND PROCESS

[75] Inventors: Eugen Konrad, Darmstadt, Fed. Rep. of Germany; Herbert Mager, Fribourg, Switzerland

[73] Assignee: Wella Aktiengesellschaft, Darmstadt, Fed. Rep. of Germany

[21] Appl. No.: 115,292

[22] Filed: Jan. 25, 1980

[30] Foreign Application Priority Data

Feb. 17, 1979 [DE] Fed. Rep. of Germany ....... 2906108

[51] Int. Cl.³ .............................................. A61K 7/13
[52] U.S. Cl. ......................................... 8/407; 8/406; 8/410; 8/411; 8/412; 8/416; 8/421; 8/424; 8/613
[58] Field of Search ...................... 8/10.2, 11, 32, 408, 8/406, 407, 410, 411, 412, 416, 421, 424, 613

[56] References Cited

U.S. PATENT DOCUMENTS

| | | | |
|---|---|---|---|
| 1,628,160 | 5/1927 | Lamb .................................. | 8/613 |
| 2,001,992 | 5/1935 | Wagner et al. ....................... | 8/424 |
| 2,094,952 | 3/1937 | Lehmann et al. ..................... | 8/410 |
| 3,337,411 | 8/1967 | Wilmsmann et al. ................. | 8/406 |
| 3,415,608 | 12/1968 | Tucker .................................. | 8/416 |
| 3,488,138 | 1/1970 | Iscowitz ................................ | 8/414 |

OTHER PUBLICATIONS

Chemical Abstracts vol. 40: 8937 & p. 7387.

Primary Examiner—Donald B. Moyer
Attorney, Agent, or Firm—Michael J. Striker

[57] ABSTRACT

A process for preparing a composition, a composition and a process for oxidative dyeing of hair are disclosed. The composition comprises at least one n,5-dihydroxy-1,2,3,4-tetrahydro-naphthalene having the general formula

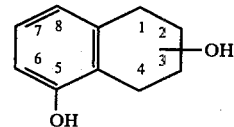

wherein n represents a number from 1,2,3, or 4, and which n,5-dihydroxy-1,2,3,4-tetrahydronaphthalene can be present as such or as a salt of an organic or inorganic base and which n,5-dihydroxy-1,2,3,4-tetrahydronaphthalene serves as a coupling compound; and at least one developer employed in hair dyeing. Intense and red tinge free blue colorations can be obtained.

18 Claims, No Drawings

HAIR DYEING COMPOSITION AND PROCESS

BACKGROUND OF THE INVENTION

1. Field of the Invention

This invention relates to a process for making a hair dyeing composition, to a hair dyeing composition and to a process of oxidative hair dyeing based on a dihydroxy-1,2,3,4-tetrahydro-naphthalene.

2. Description of the Prior Art

Oxidative dyes are important in the dyeing of hair. The color is generated by the products of the reaction of certain developers with certain coupling compounds in the presence of a suitable oxidizing agent.

Major developers include 1,4-diaminobenzene, 2,5-diaminotoluene, 3-methyl-4-aminophenol and p-aminophenol. Preferred coupling agents include alpha-naphthol, resorcinol, 4-chlororesorcinol, m-aminophenol, 5-amino-o-cresol and derivatives of m-phenylendiamine such as m-toluylendiamine and 2,4-diaminoanisol. These derivatives as well as the m-phenylendiamine itself have achieved importance as so called blue couplers based on their capability in generating blue hues by coupling oxidatively with 1,4-diaminobenzene and 1,4-diaminobenzene derivatives, respectively.

Several requirements are imposed on oxidation dyes suitable for dyeing of human hair. Such dyes have to be toxologically and dermatologically safe and they have to be capable of generating colorations of desired intensity. It is also important that a broad range of different hues can be generated by combining suitable developer and coupling components. Furthermore the obtainable hair colorations have to be fast to light, to permanent waves, to acid exposure and to rubbing. In any case, however, such hair colorations have to remain stable for at least about 4 to 6 weeks in the absence of light, of chemical agents and of rubbing.

The conventional blue couplers presently employed in hear dyeing compositions such as m-phenylenediamine, its derivatives m-toluylenediamine and 2,4-diaminoanisol as well as the more recently recommended blue couplers such as for example 1-hydroxy-3-amino-6-chlorobenzene and 2,4-diaminophenoxyethanol, are not capable of satisfactorily meeting the above mentioned requirements.

SUMMARY OF THE INVENTION

It is an object of the present invention to provide a process for making a hair dyeing composition, to provide a hair dyeing composition and to provide a process of oxidative hair dyeing which substantially provides for the above requirements.

In the following coupling compounds also called couplers described are members of the group consisting of 1,5-dihydroxy-1,2,3,4-tetrahydronaphthalene,
2,5-dihydroxy-1,2,3,4-tetrahydronaphthalene,
3,5-dihydroxy-1,2,3,4-tetrahydronaphthalene,
4,5-dihydroxy-1,2,3,4-tetrahydronaphthalene,
mixtures thereof, and salts thereof.

These compounds can alternatively be referred to by way of 5-hydroxy-(1,2,3,4)-(trihydro-, monohydroxy-)naphthalene or by way of 1,4-(3-hydroxy-m-phenylene)-n-butanol.

However, this group will be represented in the following for the purposes of readability and rapid grasping by way of a general formula set forth in the next few lines.

The present invention provides a composition for oxidative dyeing of hair comprising at least one n,5-dihydroxy-1,2,3,4-tetrahydro-naphthalene having the general formula

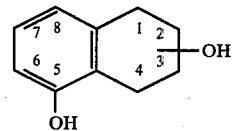

wherein n represents a number from 1, 2, 3 or 4, and which n, 5-dihydroxy-1,2,3,4-terahydro-naphthalene can be present as such or as a salt of an inorganic or an organic base and which n,5-dihydroxy-1,2,3,4-tetrahydro-naphthalene serves as a coupling compound; and at least one developer employed in hair dyeing.

There is also provided a process for preparing a composition for oxidative dyeing of hair comprising mixing at least one n, 5-dihydroxy-1,2,3,4-tetrahydro-naphthalene having the general formula

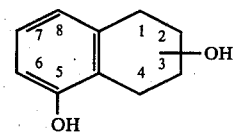

wherein n represents a number from 1, 2, 3 or 4 and which n, 5-dihydroxy-1,2,3,4-tetrahydro-naphthanlene can be employed as such or as a salt of an organic or inorganic base; and at least one developer employed in hair dyeing.

Furthermore there is provided a process for oxidative dyeing of hair comprising contacting the hair for a sufficient time and at a suitable temperature with a mixture comprising at least one n, 5-dihydroxy-1,2,3,4-tetrahydro-naphthalene having the general formula

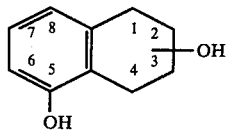

wherein n represents a number from 1, 2, 3 or 4 and which n, 5-dihydroxy-1,2,3,4-tetrahydro-naphthalene may be present as such or as a salt of an organic or inorganic base and which n, 5-dihydroxy-1,2,3,4-tetrahydro-naphthalene alone or in combination with other coupling compounds serves as a coupling compound; at least one developer employed in hair dyeing; and an oxidizing agent.

DESCRIPTION OF INVENTION AND PREFERRED EMBODIMENTS

According to the present invention, there is employed in the oxidative dyeing of hair a composition containing at least one n, 5-dihydroxy-1,2,3,4-tetrahydro-naphthalene having the general formula

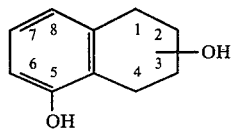

wherein n represents a number from 1, 2, 3 or 4 and which n, 5-dihydroxy-1,2,3,4-tetrahydro-naphthalene can be present as such or as a salt of an organic or inorganic base. This composition meets in an outstanding way all the requirements desirably met in an oxidative hair dyeing composition.

The dihydroxy-1,2,3,4-tetrahydro-naphthalenes of the above formula contained in the hair dyeing compositions according to the present invention and serving as coupling compounds are easily dissolvable in water in the presence of alkalies such as sodium hydroxide and they furthermore exhibit an excellent stability during storage, in particular as a component of the hair dyeing compositions of the present invention.

A preferred coupling compound for the hair dyeing compositions is 1,5-dihydroxy-1,2,3,4-tetrahydro-naphthalene. A preferred concentration of the n, 5-dihydroxy-1,2,3,4-tetrahydro-naphthalene is from about 0.01 to 3.0 weight percent. More preferred are concentrations from about 0.1 to 2.0 weight percent.

In addition, the hair dying compositions can contain other known coupling compounds such as alpha-naphthol, 3,4-diaminobenzoic acid, resorcinol, 4-chlororesorcinol, m-aminophenol, and 3-amino-6-methylphenol. Furthermore 4-oxy-1,2-methylenedioxybenzene can serve excellently as an additional coupling compound.

As a developer component of the hair dyeing compositions of the present invention are of particular interest 1,4-diamino-benzene, 2,5-diaminotoluene, p-aminophenol and 3-methyl-4-aminophenol. 2,5-diaminobenzylalcohol can also advantageously be employed as a developer in the present invention.

Both the dihydroxy-1,2,3,4-tetrahydro-naphthalenes of the above formula of the present invention as well as the conventional developer and coupling compounds can be present alone or in mixture with others in the hair dyeing compositions of the present invention.

The total concentration of developer and coupling compounds in the hair dyeing compositions of the present invention is preferably from about 0.1 to 5.0 weight percent.

In general, the developer is employed in an equimolar amount based on the coupling compound. However, no disadvantages arise in case where there is a certain excess or lack of developer from an equimolar amount.

In addition, the hair dyeing compositions of the present invention can contain other additional dyeing components, for example 6-amino-3-methylphenol, as well as conventional direct dyes, for example triphenylmethane dyes as diamond fuchsin (C.I. 42 510) and leather ruby HF (C.I. 42 520), aromatic nitro dyes such as 2-nitro-1,4-diamino-benzene and 2-amino-4-nitrophenol, azo dyes such as acid brown 4 (C. I. 14 805) and acid blue 135 (C.I. 13 385), anthraquinone dyes such as disperse red 15 (C.I. 60 710) and disperse violet 1 (C.I. 61 100) as well as 1,4,5,8-tetraamino-anthraquinone and 1,4-diamino-anthraquinone. Furthermore, there can be present in the hair dyeing compositions of the present invention additional conventional cosmetic additives, for example antioxidants such as ascorbic acid or sodium sulfite, perfume oils, complexing compounds, wetting agents, emulsifiers, thickeners, cosmetic care materials and others.

The prepared form of the hair dyeing compositions can be a solution and preferably a creme, a gel or an emulsion. The composition is a mixture of the dye components with other components conventionally employed in such compositions. As examples for conventional components of cremes, gels or emulsions are listed wetting agents or emulsifiers of the group of anionic, cationic or nonionogenic surface active substances such as fatty alcohol sulfates, alkylsulfonates, alkylbenzenesulfonates, alkyltrimethylammonium salts, ethoxylated (oxethylated) fatty alcohols, ethoxylated (oxethylated) nonylphenols, fatty acid alkanol amides, furthermore thickeners such as higher fatty alcohols, starch, cellulose derivatives, paraffin oil and fatty acids as well as in addition cosmetic care materials such as lanolin derivatives, cholesterol and pantothenic acid. The additives mentioned are employed in the usual amounts for their purpose, for example the wetting agents and emulsifiers have preferably concentrations from about 0.5 to 30 weight percent, whereas a thickener can be present in the hair dyeing composition in a concentration of from about 0.1 to 25 weight percent.

Depending on the composition, the hair dyeing compositions of the present invention can react weakly acid, neutral or weakly basic. Preferably they exhibit a pH-value in the alkaline range from about 8.0 to 11.5 and the adjustment is preferably obtained by employing suitable amounts of ammonia. However, organic amines, for example monoethanolamine or triethanolamine, can also be employed.

In the process of oxidative dyeing of hair, the hair dyeing composition, which contains a combination of developers known in the field of hair dyeing with at least one dihydroxy-1,2,3,4-tetrahydro-naphthalene of the above formula as a coupling compound as well as possibly other conventional coupling compounds, is mixed with an oxidizing agent shortly before application and this mixture is applied to the hair. As an oxidizing agent for the development of the hair coloration hydrogen peroxide is of particular interest, for example as a 6 percent aqueous solution or as an addition compound with urea, melamine or sodiumborate. The mixture is contacted with the hair for a sufficient time and at a suitable temperature and preferably for a time of from about 10 to 45 minutes and at a temperature of from about 15° C. to 50° C., with a more preferred time being from about 20 to 30 minutes. Then the hair is rinsed with water and dried. Possibly following to the rinsing the hair may be washed with a shampoo and possibly after rinsed with an aqueous solution of a weak organic acid such as for example citric acid or tartaric acid.

The preparation of the dihydroxy-1,2,3,4-tetrahydro-naphthalene contained in the hair dyeing compositions of the present invention can be performed conventionally. For example 1,5-dihydroxy-1,2,3,4-tetrahydro-naphthalene can be obtained by catalytic partial hydrogenation of 1,5-dihydroxy-naphthalene.

Regarding the possibilities of coloration, the hair dyeing compositions of the present invention based on the nature and composition of the components offer a wide range of different hues, which ranges from blond via brown, ashy, purple, violet, golden to blue and black as well as to dull hues. The colorations resulting from application of the hair dyeing compositions of the present invention are distinguished by the particular intensity of coloration.

Of considerable importance is the progress in toxicological and dermatological safety achieved with the employment of dihydroxy-1,2,3,4-tetrahydronaphthalenes of the above formula in the hair dyeing compositions of the present invention compared with conventional blue coupling compounds such as 2,4-diaminotoluene, 2,4-diaminoanisol and 1,3-diaminobenzene. While it is not wished to be bound by any theory, it is believed that the enhanced safety is based on the hydroxyl groups present on both rings and the concurrent decrease in lipid solubility.

The above described dihydroxy-1,2,3,4-tetrahydronaphthalenes provide as coupling compounds in combination with the developers 1,4-diaminobenzene and 1,4-diaminobenzene derivatives relatively cool, very intense blue hues without red component, which are not achievable with conventional coupling compounds employed in hair dyeing compositions, for example 2,4-diaminotoluene, 2,4-diaminoanisol, 2,4-diaminophenoxyethanol, 2,6-diaminotoluene, 2-amino-4-(beta-oxyethylamino)-anisol and 3-amino-6-chlorophenol.

In case the blue coupler indispensably necessary for the generation of ashy hues provides red or violet tinged blue hues with the above mentioned 1,4-diamino developers, then the obtainability of ashy colorations is either impossible or very difficult. In contrast, because of the advantageous properties of the dihydroxy-1,2,3,4-tetrahydro-naphthalenes of the present invention in generating blue hues without red components there is now no problem to dye hair in ashy natural hues.

Furthermore it has surprisingly been found that the dihydroxy-1,2,3,4-tetrahydro-naphthalenes can, as coupling compounds, even then provide very intense blue colorations when the hair dyeing compositions are in the usual liquid or gel form. Such a dyeing result was completely unexpected in view of their molecular structure comparable to that of alpha-naphthol. It is known that alpha-naphthol is of little use in liquid or gel form hair dyeing compositions, since it leads in this form of a hair dyeing composition only to unsufficient depth of color.

Finally, the hair dyeing compositions of the present invention allow to dye without problems and with hitherto unknown covering power the grayed hair which is not chemically pretreated.

EXAMPLE 1

Hair Dyeing Composition Forming a Gel

The following mixture was prepared:

| | |
|---|---|
| 0.50 g | 1,5-dihydroxy-1,2,3,4-tetrahydro-naphthalene |
| 0.70 g | 2,5-diaminotoluenesulfate |
| 0.30 g | ascorbic acid |
| 1.00 g | hydroxyethylcellulose, highly viscous |
| 5.00 g | laurylalcohol-diglycolethersulfate, sodium salt (28 percent aqueous solution) |
| 0.12 g | sodium hydroxide, solid |
| 10.00 g | ammonia, 22 percent aqueous solution |
| 82.38 g | water |
| 100.00 g | |

50 g of the above hair dyeing composition are shortly before use mixed with 50 ml of a 6 percent aqueous hydrogen peroxide solution and the mixture is then applied to blond human hair. After a developing time of from 30 to 40 minutes at about 40° C. the hair is rinsed with water and dried. The hair is colored an intense, cool blue hue.

EXAMPLE 2

Hair Dyeing Composition Forming a Gel

The following mixture was prepared:

| | |
|---|---|
| 0.08 g | 1,5-dihydroxy-1,2,3,4-tetrahydro-naphthalene |
| 0.30 g | 1,4-diaminobenzene |
| 0.25 g | resorcinol |
| 0.30 g | ascorbic acid |
| 15.00 g | oleic acid |
| 7.00 g | isopropanol |
| 0.02 g | sodium hydroxide, solid |
| 10.00 g | ammonia, 22 percent aqueous solution |
| 67.05 g | water |
| 100.00 g | |

50 g of this hair dyeing composition is mixed shortly before application with 50 ml of a six percent aqueous hydrogen peroxide solution and the mixture is allowed to act on the blond human hair for 30 minutes at about 40° C. Then the hair is rinsed with water and dried. The hair has been imparted with a naturally appearing dark ashy blond coloration.

EXAMPLE 3

Hair Dyeing Composition Forming a Creme

The following mixture was prepared:

| | |
|---|---|
| 1.40 g | 1,5-dihydroxy-1,2,3,4-tetrahydro-naphthalene |
| 1.00 g | p-aminophenol |
| 0.30 g | sodium sulfite, free of water |
| 3.50 g | laurylalcohol-diglycolethersulfate, sodium salt (28 perscent aqueous solution) |
| 15.00 g | cetylalcohol |
| 0.35 g | sodium hydroxide, solid |
| 3.00 g | ammonia, 22 percent aqueous solution |
| 75.45 g | water |
| 100.00 g | |

50 g of the hair dyeing composition are mixed shortly before application with 50 ml of a six percent aqueous hydrogen peroxide solution and the mixture is then applied to blond human hair. After an application time of 30 minutes at 40° C. the hair is rinsed with water and dried. The hair is colored rose-red.

All percentages given herein are percentages by weight unless otherwise indicated. Although the present invention has been described with respect to certain specific reagents and the like, it is to be understood that variations and modifications may be made within the scope of the invention as those skilled in the art will readily understand.

We claim:

1. A composition for oxidative dyeing of hair comprising a member of the group consisting of
   1,5-dihydroxy-1,2,3,4-tetrahydronaphthalene,
   2,5-dihydroxy-1,2,3,4-tetrahydronaphthalene,
   3,5-dihydroxy-1,2,3,4-tetrahydronaphthalene,
   4,5-dihydroxy-1,2,3,4-tetrahydronaphthalene,
   mixtures thereof, and salts thereof as a coupling compound and a developer employed in hair dyeing.

2. The composition as set forth in claim 1, wherein the developer comprises at least one of the compounds of the group consisting of 1,4-diaminobenzene, 2,5- diaminotoluene, 2,5-diaminobenzylalcohol, p-aminophenol and 3-methyl-4-aminophenol.

3. The composition as set forth in claim 1; further comprising at least one of the coupling compounds of the group consisting of alpha-naphthol, 3,4-diaminobenzoic acid, resorcinol, 4-chlororesorcinol, m-aminophenol, 4-oxy-1,2-methylenedioxybenzene and 3-amino-6-methylphenol.

4. The composition as set forth in claims 1 or 3, wherein the total concentration of coupling compound and developer is from about 0.1 to 5.0 weight percent.

5. The composition as set forth in claims 1, or 3, wherein the total concentration of coupling compound and developer is from about 0.5 to 3.0 weight percent.

6. The composition as set forth in claim 1; further comprising 6-amino-3-methylphenol as a coloring agent.

7. The composition as set forth in claim 1; further comprising direct dyes of the group consisting of diamond fuchsin (C.I. 42 510), leather ruby HF (C.I. 42 520) 2-nitro-1,4-diaminobenzene, 2-amino-4-nitrophenol, acid brown 4 (C.I. 14 805), acid blue 135 (C.I. 13 385), disperse red 15 (C.I. 60 710), disperse violet 1 (C.I. 61 100), 1,4,5,8 tetraaminoanthraquinone.

8. The composition as set forth in claim 1; further comprising an antioxidant.

9. The composition as set forth in claim 8, wherein the antioxidant is ascorbic acid or sodium sulfite.

10. The composition as set forth in claim 1; further comprising wetting agents, emulsifiers and/or thickeners.

11. The composition as set forth in claim 1 wherein the coupling compound is
1,5-dihydroxy-1,2,3,4-tetrahydronaphthalene.

12. The composition as set forth in claim 1 wherein the member of the group consisting of
1,5-dihydroxy-1,2,3,4-tetrahydronaphthalene,
2,5-dihydroxy-1,2,3,4-tetrahydronaphthalene,
3,5-dihydroxy-1,2,3,4-tetrahydronaphthalene,
4,5-dihydroxy-1,2,3,4-tetrahydronaphthalene,
mixtures thereof, and salts thereof is present in a concentration of from about 0.01 to 3 weight percent.

13. The composition as set forth in claim 12 wherein the member of the group consisting of
1,5-dihydroxy-1,2,3,4-tetrahydronaphthalene,
2,5-dihydroxy-1,2,3,4-tetrahydronaphthalene,
3,5-dihydroxy-1,2,3,4-tetrahydronaphthalene,
4,5-dihydroxy-1,2,3,4-tetrahydronaphthalene,
mixtures thereof, and salts thereof is present in a concentration of from about 0.1 to 2.0 weight percent.

14. A process for preparing a composition for oxidative dyeing of hair, comprising mixing a member of the group consisting of
1,5-dihydroxy-1,2,3,4-tetrahydronaphthalene,
2,5-dihydroxy-1,2,3,4-tetrahydronaphthalene,
3,5-dihydroxy-1,2,3,4-tetrahydronaphthalene,
4,5-dihydroxy-1,2,3,4-tetrahydronaphthalene,
mixtures thereof, and salts thereof with at least one developer employed in hair dyeing.

15. A process for oxidative dyeing of hair, comprising contacting the hair for a sufficient time and at a suitable temperature with a mixture comprising
1,5-dihydroxy-1,2,3,4-tetrahydronaphthalene,
2,5-dihydroxy-1,2,3,4-tetrahydronaphthalene,
3,5-dihydroxy-1,2,3,4-tetrahydronaphthalene,
4,5-dihydroxy-1,2,3,4-tetrahydronaphthalene,
mixtures thereof, and salts thereof, alone or in combination with other coupling compounds as a coupler; at least one developer employed in hair dyeing; and an oxidizing agent.

16. The process as set forth in claim 15, wherein the oxidizing agent is hydrogen peroxide.

17. The process as set forth in claim 15; further comprising the steps of rinsing and/or drying the hair.

18. The process as set forth in claim 15, wherein the time of contacting the hair is from about 10 to 45 minutes and wherein the temperature of contacting the hair is from about 15° to 50° C.

* * * * *